United States Patent [19]

McKinney

[11] Patent Number: 4,504,674

[45] Date of Patent: Mar. 12, 1985

[54] PROCESS FOR DIMERIZING ACRYLATES TO HEXENEDIOATES

[75] Inventor: Ronald J. McKinney, Wilmington, Del.

[73] Assignee: E. I. DuPont de Nemours & Co., Wilmington, Del.

[21] Appl. No.: 485,943

[22] Filed: Apr. 18, 1983

Related U.S. Application Data

[63] Continuation-in-part of Ser. No. 348,364, Feb. 12, 1982, abandoned.

[51] Int. Cl.$^3$ .................................. C07C 67/343
[52] U.S. Cl. ................................ 560/202; 502/162; 502/165; 502/169; 502/213; 502/226; 502/229; 502/230; 502/324; 502/329; 502/331; 562/598
[58] Field of Search ............. 560/202; 252/431 C, 252/472, 473, 474, 471; 502/162, 165, 169, 213, 226, 229, 230, 324, 329, 331

[56] References Cited

U.S. PATENT DOCUMENTS

| | | | |
|---|---|---|---|
| 2,244,645 | 6/1941 | Jacobson | 560/202 |
| 3,013,066 | 12/1961 | Alderson | 560/202 |
| 3,074,999 | 1/1963 | Rauhut et al. | 560/202 |
| 3,227,745 | 1/1966 | McClure | 560/202 |
| 3,322,819 | 5/1967 | Schreyer | 560/202 |
| 3,548,021 | 12/1970 | Brattesane | 260/465.8 D |
| 3,946,066 | 3/1976 | Todd | 260/465.8 D |
| 3,956,358 | 5/1976 | Onsager | 260/465.8 D |

FOREIGN PATENT DOCUMENTS

| | | |
|---|---|---|
| 796775 | 10/1968 | Canada . |
| 2211443 | 8/1974 | France . |
| 52-105115 | 9/1977 | Japan . |
| 1100350 | 1/1968 | United Kingdom . |
| 1355917 | 6/1974 | United Kingdom . |

*Primary Examiner*—Natalie Trousof
*Assistant Examiner*—Vera C. Clarke

[57] ABSTRACT

Alkyl acrylate esters are dimerized to dialkyl hexenedioates in the presence of a metal-treated ruthenium compound, an alcohol, optionally a phosphine, and optionally a carboxamide. The hexenedioate products are useful to prepare adipic acid.

13 Claims, No Drawings

PROCESS FOR DIMERIZING ACRYLATES TO HEXENEDIOATES

CROSS-REFERENCE TO RELATED APPLICATION

This is a continuation-in-part of copending application bearing U.S. Ser. No. 348,364, filed on Feb. 12, 1982, now abandoned.

BACKGROUND OF THE INVENTION

This invention concerns an improved ruthenium-catalyzed process for dimerizing alkyl acrylates to dialkyl hexenedioates. The latter compounds are readily convertible to adipic acid (hexanedioic acid) by hydrogenation and subsequent hydrolysis. Adipic acid is used to produce condensation polymers such as nylon 66.

Alderson, U.S. Pat. No. 3,013,066, and Alderson, Jenner, and Lindsey, *J. Am. Chem. Soc.*, 87, 5638 (1965), disclose the reaction of methyl acrylate in the presence of ruthenium chloride and methanol to give a mixture of products that includes dimethyl 2-hexenedioate.

Can. Pat. No. 796,775 discloses the dimerization of alkyl acrylates in the presence of a mixed ruthenium compound-zinc catalyst, a hydrogen donor, and a phosphine. This patent is discussed in more detail in connection with Examples M, N and 67 just preceding the claims.

SUMMARY OF THE INVENTION

This invention concerns a process for making dialkyl hexenedioates comprising dimerizing an alkyl acrylate of the formula $H_2C=CH-COOR$, wherein R is $C_1$ to $C_8$ alkyl, in the presence of a metal-treated ruthenium compound, an alcohol, optionally a phosphine, and optionally a carboxamide. The process of this invention is characterized by the fact that the alcohol component of the reaction mixture acts not as a hydrogen donor but as a promoter for the ruthenium catalyst. In this regard, see Example 67.

The process of this invention is characterized by high conversions (reactant consumed/reactant charged) and by good selectivity (mols of dimer made/mols of reactant consumed), all at relatively low reaction temperatures of about 140° C. or lower, including room temperature. This process is usually conducted at temperatures of about 50° C. to 200° C., and most preferably at about 100° C. to 150° C.

The identity of the alkyl group in the alkyl acrylate is not critical. Lower alkyl acrylates are preferred because of their availability, and methyl acrylate and ethyl acrylate are especially preferred because of ease of isolation of the reaction products. Lower alkyl is defined as alkyl of up to and including eight carbons. For practical reasons, the alkyl group will seldom exceed about 2 or 3 carbons.

The most preferred embodiment of this invention comprises contacting methyl acrylate with $RuCl_3 3H_2O$, powdered zinc, and methanol, separating the zinc, adding N-methylpyrrolidone and at least one of tri(t-butyl)phosphine, tricyclohexylphosphine, and triisopropylphosphine, and heating at about 130° C. in a closed system.

It is interesting to note that the dimerization process of this invention does not depend on presence of a hydrogen donor. None of the reactants employed in this process acts as a hydrogen donor. For instance, the alcohol component of the process acts as a promoter for the metal-treated ruthenium catalyst, not as a hydrogen donor. One of the characteristics of the instant dimerization process versus processes that employ hydrogen donors is that the concentration of saturated products produced by the instant process will seldom if ever exceed about 10 mole percent. Processes employing hydrogen donors, on the other hand, typically produce saturated dimer products approaching 90% or more.

DETAILS OF THE INVENTION

Metal-Treated Ruthenium Catalyst

The process of this invention is characterized by its use of metal-treated ruthenium compounds as catalysts. The treating metals can be added along with the ruthenium compound to the reactant mixture. Then, the reaction can be run at reaction temperatures. Alternatively, the reactant mixture including ruthenium compound, can be pretreated with the metal which is removed before applying reaction temperatures.

The ruthenium compound (as charged to the reaction mixture) can be any such compound in which the ruthenium is in an oxidation state greater than zero and is at least slightly soluble in the reaction mixture, i.e., at least about 0.01%. Usually the ruthenium compound will contain at least one more-or-less common anion associated with the ruthenium, such as halide, nitrate, sulfate, or carboxylate. For best results, it is preferred that the ruthenium compound comprise at least one chlorine atom bonded to or associated with each ruthenium atom.

Examples of operable catalysts are ruthenium dichloride, ruthenium trichloride, ruthenium tetrachloride, ruthenium tribromide, ruthenium triiodide, ruthenium nitrate, ruthenium acetate, ruthenium naphthenate, ruthenium stearate, benzeneruthenium dichloride, tris(triphenylphosphine)ruthenium dichloride, tetrakis(benzonitrile)ruthenium dichloride, benzene(triethylphosphine)ruthenium dichloride, benzene(triphenylphosphine)ruthenium dichloride, and tris(triethylphosphine)ruthenium dichloride. An especially useful catalyst is ruthenium trichloride trihydrate, which is available commercially and is readily soluble in typical reaction solutions used in the process.

The finely divided metal that is used to treat the solution containing the ruthenium compound can be zinc, manganese, iron, cobalt, or copper. Zinc gives the most active catalyst and is the metal of choice. Iron, which is about as active as the other metals, has the relative advantage of being cheaper than said other metals. The exact form of the treating metal is not critical so long as the metal is finely comminuted.

The amount of ruthenium catalyst charged will depend largely on the amount of alkyl acrylate in the reaction mixture, and the ratio of moles of alkyl acrylate to gram atoms of ruthenium can vary widely. Usually, to permit efficient use of the ruthenium catalyst, the ratio will be at least 25/1 and can be as high as 1000/1 or higher. Preferably, the ratio will be about 200/1 to 800/1, and most preferably about 250/1 to 600/1.

The amount of finely divided metal is not critical as long as an amount approximately equivalent to the ruthenium compound is present. Since excess metal can be removed by filtration or centrifugation and used again, it is convenient to use an excess of such metal. Usually about 3 to 30 gram atoms of finely divided metal per gram atom of ruthenium is used. Higher ratios can be employed, but little advantage results.

Alkanol, Phosphine, and Carboxamide

The identity of the alkanol is not critical. Normally, the alkanol will be the one in which the alkyl group is the same as the alkyl group in the alkyl acrylate. This eliminates formation of mixed esters through ester interchange. Lower alkanols can be employed including branched alcohols such as isopropanol and the like. The preferred alkanols are methanol and ethanol.

Alkanols have been found to act as catalyst promoters in the process of this invention. For that purpose, they are effective at low concentrations relative to catalyst. Although concentrations even lower than 1 mol of alkanol per gram atom of ruthenium can be employed, it is convenient to use about 1 to 5 mols of alkanol per gram atom of ruthenium. The actual amount can be adjusted to give the desired balance between dimer formation and by-product formation. The upper limit is a practical one and there appears to be no incentive for employing more than 100 mols of alkanol per gram atom of ruthenium. Such low alkanol levels are consistent with their promoters as catalyst promoters not as hydrogen donors.

One way to use the alkanols in the process of this invention is to contact them with ruthenium compound and treating metal in the absence of alkyl acrylate. Excess alkanol above the amount necessary to treat the catalyst can then be removed before dimerization. Of course, excess alkanol need not be removed, nor must the catalyst be contacted with alkanol outside the presence of other reactants and optional ingredients. Because alkanols are not harmful to the dimerization they can be, but need not be, present during the reaction.

It has also been found that the production of dimers in this process can be increased by incorporating a selected tertiary phosphine in the reaction mixture. The optimum amount of phosphine relative to ruthenium varies with the identity of the phosphine. Usually, at least about 0.5 mol of phosphine per gram atom of ruthenium is present and preferably about 1 to 3 mols. Higher ratios can be used, but usually at the expense of decreased dimer formation.

Operable phosphines include trialkylphosphines, tricycloalkylphosphines, and triarylphosphines. Preferred are tri(lower alkyl)phosphines, tricycloalkylphosphines in which each cycloalkyl group contains 5 to 7 carbons, and triarylphosphines in which each aryl group contains from 6 to 12 carbons. Examples are trimethylphosphine, triethylphosphine, triisopropylphosphine, tri(s-butyl)phosphine, tri(t-butyl)phosphine, tri(t-pentyl)phosphine, tris(2-ethylhexyl)phosphine, tricyclopentylphosphine, tricyclohexylphosphine, tricycloheptylphosphine, triphenylphosphine, trinaphthylphosphine, and tris(biphenylyl)phosphine. Tricyclohexylphosphine and trialkylphosphines in which the alkyl groups are secondary or tertiary are most preferred, since their beneficial effect on the ruthenium catalyst is the greatest.

A method for selecting phosphines that will work well in the present process is by their cone angles, preferred phosphines having cone angles greater than about 150°. Cone angles and the method for measuring them are discussed by Tolman in *J. Am. Chem. Soc.*, 92, 2956 (1970) and 96, 53 (1974). Cone angles for typical operable phosphines are as follows: triethylphosphine, 132°; triisopropylphosphine, 160°; tricyclohexylphosphine, 170°; and tri(t-butyl)phosphine, 182°.

Carboxamide cosolvents can be employed if desired. In fact, it has been found that the selectivity of the process can be increased by adding dimethylformamide (DMF) or N-methylpyrrolidone (NMP) to the reaction mixture. The higher selectivity appears both as an increase in the ratio of dimers to trimers formed and in the ratio of linear dimers to nonlinear dimers. Trimers and nonlinear dimers are less desirable products, since they cannot be converted directly to adipic acid. Occasionally, a minor amount of dialkyl 2,4-hexadienoate is found in the products. Such compounds are also directly convertible to adipic acid, and are embraced in the term "linear dimers".

Operable cosolvents include acyclic aliphatic carboxamides of up to about eight carbons and intracyclic aliphatic carboxamides of up to about 16 carbons. Examples are diethylformamide, dipropylformamide, dimethylacetamide, dipropylacetamide, N-butylpyrrolidone, N-(2-ethylhexyl)pyrrolidone, and N-dodecylpyrrolidone.

The amount of cosolvent, when one is used, is usually about 0.5 to 5 times the volume of the reaction mixture to which it is added, and preferably between about 1 to 2 times the volume of the mixture.

Minor amounts of an inhibitor such as hydroquinone and the like can be added to the reaction mixture to insure against polymerization of the alkyl acrylate. The process of this invention can be run in a batch operation, as illustrated in the Examples, or continuously.

EXAMPLES

The following Examples illustrate the process of the invention. All preparative manipulations were carried out under an atmosphere of purified nitrogen in a Vacuum/Atmosphere Corp. dry box. Reagents were not specially purified unless otherwise noted. Many of the reaction mixtures, prepared as described, were sealed by torch in heavy-walled glass ampoules under vacuum at liquid-nitrogen temperature (outside the dry box) and then submerged in a thermostated oil bath ($\pm 1°$ C.) for specified periods. Each ampoule was then cooled in an ambient-temperature water bath and opened to the air, whereby the reaction was completely quenched.

The quenched reaction mixtures were analyzed by gas chromatography (GC), [HP5710A, FID; column, 10% SE30 on 80/90 mesh "Anakrom" ABS, 12'×⅛" (3.6 m×3.2 mm) (Supelco)], and product concentrations calculated by applying appropriate response factors and comparing integrated area of products with that of the internal standard decane (nonane in Examples 64, 65 and 66). Approximate response factors were determined by mixing known amounts of methyl acrylate, dimethyl adipate, decane and dimethylformamide in various combinations and analyzing by GC. A distilled sample of a mixture of dimers was found to have essentially the same response factor as dimethyl adipate.

Identity of the products was determined by mass spectral analysis of gas chromatographic effluent (GC-MS), and for isomers by comparing of GC retention times against those of authentic samples. When pertaining to a reactant and not to a specified product, the term "conversion", expressed in percent, is defined as 100×(reactant charged−reactant remaining)/reactant charged.

EXAMPLE 1

A round-bottom flask was charged with ruthenium trichloride trihydrate (RuCl$_3$·3H$_2$O) (0.26 g; 1.0 mmol), methyl acrylate (5 cc; 55 mmol), methanol (20 cc) and powdered zinc (0.25 g; 3.8 mmol) and the mixture was stirred for 2.5 h. Analysis of the solution by gas chromatography revealed that small amounts of methyl acrylate dimers (linear and nonlinear) had been formed.

EXAMPLE 2

This Example shows that the presence of an alkanol during treatment of the ruthenium compound by the finely divided metal is essential or at least highly desirable.

A mixture of $RuCl_3 \cdot 3H_2O$ (0.26 g; 1.0 mmol), methyl acrylate (20 cc; 220 mmol) and powdered zinc (0.30 g; 4.6 mmol) was stirred at 55° C. for 0.5 h. GC analysis showed no dimer. Methanol (0.5 cc) was added, to give an immediate lightening of color. The GC analysis after a few minutes showed the presence of methyl acrylate dimers and dimethyl 2,4-hexadienoate.

EXAMPLE 3

A mixture of $RuCl_3 \cdot 3H_2O$ (0.26 g; 1.0 mmol), methanol (5 cc), methyl acrylate (25 cc; 275 mmol) and powdered zinc (0.30 g; 4.6 mmol) was stirred for 0.5 h and filtered. The filtrate was heated in a pressure bottle at 125° C. for 16 h. GC analysis showed about 30% conversion of methyl acrylate, with products about equally divided between dimers and trimers (confirmed by mass-spectral analysis).

EXAMPLES 4 TO 8

A solution comprised of $RuCl_3 \cdot 3H_2O$ (0.60 g; 2.3 mmol), methyl acrylate (60 cc; 660 mmol), methanol (5 cc), decane (0.50 cc; an internal GC standard), and hydroquinone (0.50 g) was prepared. Each of 10-cc aliquots of this solution was treated with powdered zinc, manganese, iron, copper, or cobalt for 1 h, and the excess metal was removed by filtration. The activities of the resulting mixtures were compared against that of the parent mixture by heating at 140° C. for 3 h and analyzing by GC. The results are recorded in the following table with the notation "mol/Ru" meaning mols of compound(s) per gram atom of ruthenium.

| Example | Added Metal | Dimers, mol/Ru |
|---|---|---|
| | None | 2.1 |
| 4 | Manganese | 6.4 |
| 5 | Iron | 6.1 |
| 6 | Cobalt | 5.5 |
| 7 | Copper | 6.5 |
| 8 | Zinc | 24 |

Examples 9 to 37 explore the effects of varying the amount of phosphine relative to the amount of ruthenium.

EXAMPLES 9 TO 26 AND COMPARISONS A TO C

A mixture of $RuCl_3 \cdot 3H_2O$ (1.04 g; 4.0 mmol), methanol (8 cc), methyl acrylate (160 cc; 1760 mmol), decane (4.00 cc) and powdered zinc (2.0 g) was stirred for 1.5 h and filtered. Aliquots (3 cc each) of this catalyst solution were treated with a variety of phosphines and sealed under vacuum in glass ampoules. Each reaction mixture was heated at 125° C. in an oil bath for 20.5 h, and then analyzed by GC. Additional experiments with phosphines were carried out under identical conditions on aliquots of a reaction mixture equivalent to the one described above. The combined results are in the following table.

| Example | Phosphine | Amount, mol/Ru | Dimers mol/Ru | Trimers mol/Ru |
|---|---|---|---|---|
| 9 | None | — | 27 | 10 |
| 10 | None | — | 25 | 8 |
| 11 | Trimethylphosphine | 1 | 23 | 10 |
| 12 | Trimethylphosphine | 2 | 70 | 15 |
| 13 | Triethylphosphine | 1 | 45 | 11 |
| 14 | Triethylphosphine | 2 | 77 | 15 |
| 15 | Triethylphosphine | 3 | 20 | 6 |
| 16 | Triethylphosphine | 4 | 49* | 9 |
| 17 | Triphenylphosphine | 0.5 | 40 | 11 |
| 18 | Triphenylphosphine | 1 | 78 | 14 |
| 19 | Triphenylphosphine | 2 | 71 | 13 |
| 20 | Triphenylphosphine | 3 | 35 | 7 |
| 21 | Triphenylphosphine | 4 | 37 | 7 |
| 22 | Triisopropylphosphine | 0.5 | 52 | 13 |
| 23 | Triisopropylphosphine | 1 | 130 | 15 |
| 24 | Triisopropylphosphine | 1.5 | 103 | 16 |
| 25 | Triisopropylphosphine | 2.5 | 97 | 21 |
| 26 | Triisopropylphosphine | 3.5 | 91* | 17 |
| A | Trimethyl phosphite | 1 | 31 | 8 |
| | Trimethyl phosphite | 2 | 21 | 5 |
| | Trimethyl phosphite | 5 | 2 | 4 |
| B | Triisopropyl phosphite | 1 | 28 | 8 |
| | Triisopropyl phosphite | 4 | 25 | 10 |
| C | Triphenyl phosphite | 1 | 7 | 3 |
| | Triphenyl phosphite | 4 | 1 | 1 |

*Less than 50% linear dimer.

The foregoing table shows that use of the phosphites of Comparisons A, B, C give results which are little better than, and in some cases not as good as, can be achieved with no phosphorus-containing compound. Such results are clearly inferior to those obtained with the described phosphines.

EXAMPLES 27 TO 37

In a manner similar to that of Examples 9 to 26, a reaction mixture was prepared from $RuCl_3 \cdot 3H_2O$ (1.04 g, 4.0 mmol), methanol (8 cc), methyl acrylate (155 cc, 1705 mmol), decane (8.00 cc) and powdered zinc (2 g). Aliquots were treated with phosphines and heated at 120° C. for 16 h. Results are in the following table.

| Example | Phosphine | Amount, mol/Ru | Dimers mol/Ru | Trimers mol/Ru |
|---|---|---|---|---|
| 27 | None | — | 25 | 8 |
| 28 | Triethylphosphine | 1 | 45 | 9 |
| 29 | Triethylphosphine | 2 | 70 | 13 |
| 30 | Triethylphosphine | 3 | 26 | 8 |
| 31 | Triisopropylphosphine | 0.7 | 75 | 10 |
| 32 | Triisopropylphosphine | 1.1 | 107 | 14 |
| 33 | Triisopropylphosphine | 1.5 | 100 | 14 |
| 34 | Triisopropylphosphine | 2.5 | 73* | 12 |
| 35 | Tri(t-butyl)phosphine | 1.2 | 71 | 14 |
| 36 | Tri(t-butyl)phosphine | 2.1 | 133 | 11 |
| 37 | Tri(t-butyl)phosphine | 3.0 | 137 | 10 |

Less than 50% linear dimer.

EXAMPLES 38 AND 39 AND COMPARISONS D AND E

These Examples show the effects of adding zinc, a phosphine, or both to an $RuCl_3$ catalyst system like that of U.S. Pat. No. 3,013,066.

A reaction mixture was prepared by mixing $RuCl_3 \cdot 3H_2O$ (0.60 g; 2.3 mmol), methyl acrylate (45 cc; 495 mmol), methanol (15 cc; 372 mmol), hydroquinone (0.60 g), and decane (2.00 cc) for 0.5 h. Aliquot I (10 cc) was set aside, and the remaining solution was treated with powdered zinc (1 g) for 1 h and then filtered. Aliquot II (10 cc) was set aside and the remaining solution was treated with triisopropylphosphine (0.32 g; 2.0 mmol) to make mixture III. A sample of each mixture was heated in a sealed tube at 140° C. for 3 h and then analyzed by GC. Similarly, a solution equivalent to mixture I was treated with triisopropylphosphine (0.07 g) and a sample of the treated mixture was heated at 140° C. for 3 h. The amounts of dimer product are recorded in the following table wherein PR₃ refers to triisopropylphosphine.

| Example | Reaction Mixture | Dimers (mol/Ru) | Trimers (mol/Ru) | Methyl Propionate (mol/Ru) | Methyl β-Methoxy-propionate (mol/Ru) |
|---|---|---|---|---|---|
| D | I | 2.8 | 0.4 | 1 | 1 |
| 38 | II (I + Zn) | 29 | 6 | 28 | 3 |
| 39 | III (II + PR₃) | 61 | 5 | 20 | 25 |
| E | I + PR₃ | 0.9 | 0.2 | — | — |

EXAMPLES 40 TO 43 AND COMPARISONS F TO L

A mixture of RuCl₃·3H₂O (0.13 g; 0.5 mmol), methanol (1 cc), methyl acrylate (25 cc; 275 mmol) and excess powdered zinc was stirred for 0.5 h and filtered. The filtrate was treated with triisopropylphosphine (0.12 g; 0.75 mmol), decane (1.00 cc) and hydroquinone (0.1 g). To each of 1-cc aliquots of this suspension was added 2 cc of dimethylformamide, N-methylpyrrolidone, or methyl acrylate. The resulting mixtures were heated at 130° C. for 4 h and then analyzed by GC. The product yields and distribution are found in the following table. The notation "Lin/Nonlin" means the ratio of linear dimers to nonlinear dimers formed.

| Example | Solvent | Dimers mol/Ru | Dimers Lin/Nonlin | Trimers mol/Ru |
|---|---|---|---|---|
| 40 | Dimethylformamide | 77 | 3 | 3.5 |
| 41 | N—methylpyrrolidone | 100 | 16 | 5.4 |
| 42 | Methyl acrylate | 105 | 1 | 17.5 |
| 43 | None | 90 | 1 | 8.8 |

Dimethylformamide and N-methylpyrrolidone, especially the latter, increased the linear/nonlinear dimer ratio, both solvents decreasing the amount of trimers formed relative to dimers.

By the method of Examples 40 to 43, alternative cosolvents were employed. As shown in the following table, such cosolvents produced generally poorer selectivities, lower Lin/Nonlin ratios, or both.

| Example | Solvent | Dimers mol/Ru | Dimers Lin/Nonlin | Trimers mol/Ru |
|---|---|---|---|---|
| F | Toluene | 46 | 0.6 | — |
| G | Ethyl Acetate | 85 | 0.6 | 2.2 |
| H | Tetrahydrofuran | 49 | 0.6 | 2.6 |
| I | 2-Butanone | 28 | 0.6 | 1.9 |
| J | Acetonitrile | 22 | 0.6 | 3.2 |
| K | Pyridine | 47 | 0.1 | — |
| L | Dimethyl sulfoxide | 27 | 0.1 | — |

EXAMPLES 44 TO 49

Random samples of dimer mixtures made generally as described in Example 41 were hydrogenated in ethyl acetate over palladium on carbon at ambient temperature and 20 psig (138 kPa), and the relative amounts of dimethyl adipate and dimethyl α-methylglutarate were determined by GC. These determinations showed:

| Example | Phosphine | % Linear Dimer |
|---|---|---|
| 44 | None | 94 |
| 45 | Triethylphosphine | 97 |
| 46 | Triisopropylphosphine | 98 |
| 47 | Tri(t-butyl)phosphine | 90 |
| 48 | Tricyclohexylphosphine | 90 |
| 49 | Tricyclohexylphosphine | 96 |

EXAMPLES 50 TO 52

These Examples show the effects of varying the order of addition of the components of the reaction mixture.

Example 50

A reaction mixture was prepared by mixing RuCl₃·3H₂O (0.13 g; 0.5 mmol), methanol (1 cc), methyl acrylate (25 cc; 275 mmol) and excess powdered zinc for 0.5 h and filtering. The filtrate was treated with triisopropylphosphine (0.08 g; 0.5 mmol), N-methylpyrrolidone (25 cc), decane (1 cc) and hydroquinone (0.1 g). Aliquots (3 cc) were sealed under vacuum and heated at 130° C., and samples were removed at intervals. The amounts of dimers formed are recorded in the table below. Hydrogenation of the 300 min sample over Pd/C showed that the dimer fraction was 89% linear; i.e., the linear/nonlinear ratio was 8.1/1.

Example 51

A reaction mixture was similarly prepared except that the triisopropylphosphine was present during the treatment with zinc. The results are found in the table. Hydrogenation of the 300 min sample showed that the dimer formed was 89% linear.

Example 52

A reaction mixture was similarly prepared except that all reagents were present during the treatment with zinc and the mixing occurred for 45 minutes before filtering. The results are found in the table. Hydrogenation of the 300 min sample showed the dimer was 79% linear; i.e., the linear/nonlinear ratio was 3.8/1.

| Example | Time, min | Dimers, mol/Ru | Trimers, mol/Ru |
|---|---|---|---|
| 50 | 60 | 30 | 2 |
|  | 180 | 90 | 5 |
|  | 300 | 135 | 10 |
| 51 | 60 | 20 | 2 |
|  | 180 | 57 | 4 |
|  | 300 | 93 | 8 |
| 52 | 60 | 30 | 4 |
|  | 180 | 60 | 8 |
|  | 300 | 117 | 10 |

EXAMPLES 53 TO 66

These Examples show that the production of dimers increases with increasing amounts of alkanol.

A reaction mixture was prepared by mixing RuCl₃·3H₂O (0.13 g; 0.5 mmol), methanol (1 cc), methyl acrylate (25 cc; 275 mmol), and excess powdered zinc for 0.5 h and then filtering. The filtrate was treated with triisopropylphosphine (0.12 g; 0.8 mmol), methyl acrylate (25 cc), decane (1.00 cc) and hydroquinone (0.1 g). Aliquots (2.5 cc) were treated with increasing amounts of methanol and the resulting mixtures were heated at 130° C. for 3 h. Similar reactions were carried out in which N-methylpyrrolidone (25 cc) replaced the second charge of methyl acrylate. The following table summarizes results.

| Example | cc Methanol Added | Dimers Mol/Ru | Methyl Propionate | Methyl $\beta$-Methoxy-propionate |
|---|---|---|---|---|
| 53 | None | 64 | — | 0 |
| 54 | 0.25 | 116 | 16 | 7 |
| 55 | 0.50 | 128 | 17 | 14 |
| 56 | 0.75 | 148 | 21 | 20 |
| 57 | 1.00 | 163 | 23 | 39 |
| Runs with N—methylpyrrolidone: | | | | |
| 58 | None | 71 | 2 | 1 |
| 59 | 0.25 | 65 | 2 | 12 |
| 60 | 0.50 | 61 | 2 | 25 |
| 61 | 0.75 | 65 | 5 | 35 |
| 62 | 1.00 | 72 | 8 | 42 |

EXAMPLE 63

A catalyst solution was prepared by mixing $RuCl_3 \cdot 3H_2O$ (0.13 g, 0.5 mmol), methanol (1 cc), methyl acrylate (25 cc, 275 mmol) and excess powdered zinc for 0.5 hr and filtering. The filtrate was treated with tricyclohexylphosphine (0.21 g, 0.75 mmol), N-methylpyrrolidone (25 cc), decane (1.00 cc) and hydroquinone (0.1 g). Aliquots were sealed under vacuum and heated to 130° C. Results are shown below.

| Time, min | Dimers, mol/Ru | Trimers, mol/Ru |
|---|---|---|
| 60 | 40 | 1 |
| 150 | 113 | 4 |
| 270 | 167 | 7 |

EXAMPLE 64

A catalyst solution was prepared by mixing benzene(triisopropylphosphine)ruthenium dichloride (0.10 g, 0.25 mmol), methanol (0.5 cc), methyl acrylate (13 cc) and excess powdered zinc for 1 hr and filtering. The filtrate was treated with N-methylpyrrolidone (13 cc), nonane (0.50 cc; internal standard), and hydroquinone (0.05 g). The mixture was sealed in glass under vacuum and heated at 130° C. for 3 hr. GC analysis showed the presence of dimers (45 mol/Ru) and trimers (5 mol/Ru).

EXAMPLE 65

A catalyst solution was prepared by mixing ruthenium tris(acetylacetonate) (0.10 g), methanol (0.5 cc), methyl acrylate (13 cc), N-methylpyrrolidone (12 cc), nonane (0.50 cc), hydroquinone (0.05 g) and excess powdered zinc for 1 hr and filtering. The filtrate was sealed in glass under vacuum and heated at 130° C. for 2.5 hr. GC analysis showed the presence of dimers (40 mol/Ru) and trimers (6 mol/Ru).

EXAMPLE 66

In a manner similar to that of Example 65, a catalyst solution was prepared with ruthenium tribromide (0.09 g) replacing ruthenium tris(acetylacetonate), except the mixture was stirred for 2.5 hr before filtering, and heated for 3 hr at 130° C. GC analysis showed the presence of dimers (8 mol/Ru) and trimers (2 mol/Ru).

COMPARISONS M AND N

These Comparisons show that the catalytic dimerization described herein does not occur with two monomers, acrylonitrile and methyl methacrylate, which are not reactants of the invention but which are contemplated for use in the processes of U.S. Pat. No. 3,013,066 and Can. Pat. No. 796,775. That the instant process does not work with these two monomers (which are preferred reactants of the Canadian Patent) indicates the dissimilarity between the process of these patents and the process of this invention.

Comparison M

A reaction mixture was prepared by mixing $RuCl_3 \cdot 3H_2O$ (0.13 g; 0.5 mmol), methanol (0.5 cc), N-methylpyrrolidone (10 cc), acrylonitrile (5 cc), hydroquinone (0.10 g) and excess powdered zinc for 1 hr and filtering. During this period, the color changed from deep brown to amber. Aliquots (3 cc) were sealed under vacuum and heated at 140° C., and samples were removed at intervals and analyzed by GC. No dimers were detected after 2 hrs.

Comparison N

A reaction mixture was prepared by mixing $RuCl_3 \cdot 3H_2O$ (0.13 g; 0.5 mmol), methanol (0.5 cc), methyl methacrylate (15 cc) and excess powdered zinc for 0.5 hr and then filtering. No color change occurred during this period. To the filtrate was added triisopropylphosphine (0.08 g; 0.75 mmol), N-methylpyrrolidone (15 cc), decane (1.00 cc) and hydroquinone (0.10 g). Aliquots (3 cc) were sealed under vacuum and heated at 130° C. and samples removed at intervals and analyzed by GC. After 3 hrs, no dimer products were observed.

EXAMPLE 67

This Example shows that the alcohol component employed in the process of this invention does not act as a hydrogen donor. This fact explains why the dimerized product produced by the process of this invention contains little, if any, hydrogenated product whereas the process of Can. Pat. No. 796,775 produces saturated products (hydrodimers) predominantly.

A solution comprised of $RuCl_3 \cdot 3H_2O$ (0.13 g; 0.5 mmol), methyl acrylate (10 cc; 110 mmol) and methanol (1 cc) was treated with zinc powder (1 g) for 0.5 hr. The excess zinc was removed by filtration. The volatiles, including methanol were removed under vacuum. The solid residue was dried under high vacuum (0.1 Torr) for 1 hr.

The residue was redissolved in methyl acrylate (25 cc; 275 mmol) and naphthalene (0.50 g) was added as an internal standard. Thus, there was no methanol present during the dimerization process. Aliquots were heated in sealed glass ampoules at 140° C. and then analyzed by gas chromatography at intervals as follows:

| Time (Hours) | Dimer (Mol/Ru) |
|---|---|
| 1.5 | 19 |
| 3.0 | 33 |
| 4.5 | 46 |
| 5.7 | 63 |

The embodiments of the invention in which an exclusive property or privilege is claimed are defined as follows:

1. A ruthenium-catalyzed process for making dialkyl hexenedioates in the absence of a hydrogen donor consisting essentially of dimerizing an alkyl acrylate of the formula $H_2C=CH-COOR$, wherein R is $C_1$ to $C_8$ alkyl, in the presence of an alcohol acting as catalyst promoter, said alcohol present at a concentration of no more than 100 mols per gram atom of ruthenium, and a ruthenium compound treated with one or more metals selected from the group consisting of zinc, manganese, iron, cobalt, and copper, said ruthenium compound being in an oxidation state greater than zero, there being present optionally a phosphine and optionally a carboxamide cosolvent.

2. A process according to claim 1 wherein the metal is zinc.

3. A process according to claim 1 wherein the ruthenium compound is ruthenium trichloride trihydrate.

4. A process according to claim 1 wherein the alcohol is selected from the group consisting of methanol and ethanol.

5. A process according to claim 1 conducted in the presence of a phosphine.

6. A process according to claim 5 wherein the phosphine is a trialkylphosphine or a tricycloalkylphosphine.

7. A process according to claim 6 wherein the phosphine is selected from the group consisting of tri(t-butyl)phosphine, triisopropylphosphine, and tricyclohexylphosphine.

8. A process according to claim 1 conducted in the presence of a carboxamide cosolvent.

9. A process according to claim 8 wherein the cosolvent is selected from the group consisting of dimethylformamide and N-methylpyrrolidone.

10. A process according to claim 9 wherein the treating metal is zinc, the phosphine is tricyclohexylphosphine, and the cosolvent is N-methylpyrrolidone.

11. A process according to any of claims 1 to 10 wherein R is methyl and the alcohol is methanol.

12. A process according to any of claims 1 to 10 wherein R is ethyl and the alcohol is ethanol.

13. A process according to claim 1 consisting essentially of contacting methyl acrylate with $RuCl_3 \cdot 3H_2O$, powdered zinc, and methanol, separating the zinc, adding N-methylpyrrolidone and at least one of tri(t-butyl)phosphine, tricyclohexylphosphine, and triisopropylphosphine, and additionally heating at about 130° C. in a closed system.

* * * * *